United States Patent [19]

Schmalstieg et al.

[11] Patent Number: 5,723,564
[45] Date of Patent: Mar. 3, 1998

[54] PROCESS FOR PREPARING ISOCYANURATE GROUP-CONTAINING POLYISOCYANATES AND THEIR USE IN TWO-COMPONENT COATING COMPOSITIONS

[75] Inventors: Lutz Schmalstieg, Köln; Carl-Gerd Dieris, Dormagen; Wolfgang Kremer, Kerken; Bernd Riberi, Odenthal, all of Germany

[73] Assignee: Bayer Aktiengesellschaft, Leverkusen, Germany

[21] Appl. No.: 667,568

[22] Filed: Jun. 21, 1996

[30] Foreign Application Priority Data

Jun. 29, 1995 [DE] Germany .............. 195 23 657.2

[51] Int. Cl.$^6$ .................................................. C08G 18/79
[52] U.S. Cl. ............ 528/73; 252/182.22; 544/193; 544/221; 544/222; 528/49
[58] Field of Search ................ 528/73, 49; 252/182.22; 544/221, 222, 193

[56] References Cited

U.S. PATENT DOCUMENTS

| | | | |
|---|---|---|---|
| 3,996,223 | 12/1976 | Gupta et al. | 260/248 NS |
| 5,064,960 | 11/1991 | Pedain et al. | 544/222 |
| 5,369,207 | 11/1994 | Wolff et al. | 528/49 |

FOREIGN PATENT DOCUMENTS 1458564  12/1976  United Kingdom.

*Primary Examiner*—Rachel Gorr
*Attorney, Agent, or Firm*—Joseph C. Gil; Thomas W. Roy

[57] ABSTRACT

A process for the preparation of isocyanurate group-containing polyisocyanates in solvents which are inert towards isocyanate groups by reacting 0.2 to 1.5% of the isocyanate groups of diisocyanatotoluene with an aliphatic monohydric alcohol having 6 to 22 carbon atoms and subsequently trimerizing at least a portion of the isocyanate groups of the urethanized diisocyanates in the form of 40 to 70 wt. % solutions in lacquer solvents which are inert towards isocyanate groups, and the use of these polyisocyanates in two-component polyurethane coating compositions.

9 Claims, No Drawings

PROCESS FOR PREPARING ISOCYANURATE GROUP-CONTAINING POLYISOCYANATES AND THEIR USE IN TWO-COMPONENT COATING COMPOSITIONS

BACKGROUND OF THE INVENTION

1. Field of the Invention

The present invention relates to an improved process for preparing solutions of polyisocyanates which contain isocyanurate groups, are based on diisocyanatotoluenes and have a concentration of free diisocyanatotoluene of less than 0.1%, and to the use of these solutions for preparing two-component polyurethane coating compositions.

2. Description of the Prior Art

Isocyanurate group-containing polyisocyanates, which are prepared from 2,4- and optionally 2,6-diisocyanatotoluene, represent useful components for two-component polyurethane coating compositions for coating wood and furniture. The preparation of these modified polyisocyanates is generally achieved by partial trimerization of the isocyanate groups in 2,4- and optionally 2,6-diisocyanatotoluene that are present as 30 to 70 wt. % solutions in suitable lacquer solvents. These polyisocyanates are described, for example, in DE-OS 2,414,413, DE-OS 2,452,532 and DE-OS 3,928,503.

These prior publications also describe solutions of isocyanurate group-containing polyisocyanates which have a residual concentration of free diisocyanatotoluene, i.e., a free monomer content, of 0.1%. This low free monomer content can be obtained at a high degree of trimerization, but this also leads to a drastically increased viscosity which is a disadvantage from an ecological point of view.

A further possibility for producing particularly low free monomer contents is post-urethanization as described in DE-OS 2,414,413. Post-urethanization, however, is also associated with a considerable increase in viscosity.

Therefore, an object of the present invention is to prepare solutions of isocyanurate group-containing polyisocyanates, which are prepared from diisocyanatotoluene, have a free monomer content of of less than 0.1 wt. % and have a low viscosity.

This object may be obtained by urethanizing the diisocyanatotoluene used as starting diisocyanate with very small amounts of long chain monoalcohols before production of the trimer and then subjecting the urethanized starting diisocyanates in the form of 40 to 70 wt. % solutions in suitable lacquer solvents to partial trimerization until the concentration of free starting diisocyanate has fallen to below 0.1 wt. %.

SUMMARY OF THE INVENTION

The present invention relates to an improved process for preparing isocyanurate group-containing polyisocyanates in lacquer solvents which are inert towards isocyanate groups by a) reacting 0.2 to 1.5% of the NCO groups of a diisocyanate component containing
  i) 80 to 100 wt. %, based on the weight of the mixture, of 2,4-diisocyanatotoluene and
  ii) up to 20 wt. %, based on the weight of the mixture, of 2,6-diisocyanatotoluene,
with a monohydric alcohol, R—OH, wherein R represents a linear or branched, saturated or unsaturated, aliphatic hydrocarbon group with 6 to 22 carbon atoms, to form urethanized diisocyanates, b) trimerizing at least a portion of the isocyanate groups of the urethanized diisocyanates in the form of 40 to 70 wt. % solutions in lacquer solvents which are inert towards isocyanate groups and in the presence of a catalyst for accelerating the trimerization of isocyanate groups, and c) terminating the trimerization reaction by adding a catalyst poison to obtain a reaction mixture having a free diisocyanatotoluene content of less than 0.1 wt. %, based on the weight of the reaction mixture.

The invention also relates to two-component polyurethane coating compositions containing these isocyanurate group-containing polyisocyanate solutions.

DETAILED DESCRIPTION OF THE INVENTION

It is known from DE-OS 3,928,503 that 2,4-diisocyanatotoluene and mixtures thereof with 2,6-diisocyanatotoluene can be modified by urethanization of a portion of the isocyanate groups followed by trimerization of more of the isocyanate groups to obtain products having an improved capacity for dilution by aromatic compounds. According to this reference, relatively high proportions of diisocyanate, i.e., 2.5% to 7% of the NCO groups, are subjected to urethanization. However, this large amount of urethanization dramatically impairs the drying characteristics of the polyisocyanates.

It has to be regarded as extremely surprising that the modification according to the invention, which uses very small amounts of monoalcohol, causes such a significant effect with respect to the free monomer content and the viscosity of the resulting products, especially since the disclosure in DE-OS 3,928,503 does not mention this effect, despite the use of relatively large amounts of alcohol.

The process according to the invention differs from the process in DE-OS 3,928,503 both with regard to the objects to be obtained and with regard to the steps taken in order to achieve these objects.

The starting material for the process according to the invention is 2,4-diisocyanatotoluene or mixtures thereof with up to 20 wt. %, based on the weight of the mixture, of 2,6-diisocyanatotoluene. The use of pure 2,4-diisocyanatotoluene is preferred.

At least the second stage of the process according to the invention is performed in the presence of lacquer solvents which are inert towards isocyanate groups. Examples of these solvents include ethyl acetate, n-butyl acetate, methylethyl ketone, methylisobutyl ketone, methoxypropyl acetate and mixtures of solvents of this type.

In the first stage of the process according to the invention 0.2 to 1.5%, preferably 0.2 to 1%, of the isocyanate groups of the dissolved diisocyanate initially present are reacted with a monohydric alcohol or a mixture of monohydric alcohols described hereinafter.

Suitable monohydric alcohols are those corresponding to the formula

R—OH wherein R represents a linear or branched, saturated or unsaturated, aliphatic hydrocarbon group with 6 to 22, preferably 8 to 18 carbon atoms. Examples of suitable monohydric alcohols include 1-hexanol, 1-octanol, 2-ethylhexanol, 1-decanol, 1-dodecanol, 1-tetradecanol, stearyl alcohol, linoleyl alcohol, oleyl alcohol, behenyl alcohol. 1-dodecanol is especially preferred.

In the first stage in the process according to the invention 0.2 to 1.5, preferably 0.2 to 1%, of the isocyanate groups of the starting diisocyanate are urethanized by reacting with a monohydric alcohol or a mixture of monohydric alcohols. This reaction of the diisocyanate and monoalcohol is performed at about 0° to 120° C., preferably 20° to 80° C., in presence or absence of the previously mentioned solvents. The solvent serves as a reaction medium for the trimerization reaction following urethanization. In the case of urethanization reaction is conducted in the absence of a solvent, the partially urethanized starting diisocyanate is dissolved in a solvent or solvent mixture before trimerization.

Subsequent trimerization of the isocyanate groups is performed in a catalytic manner at 20° to 80° C. using 40 to 70 wt. % solutions of the urethanized starting diisocyanate are used.

Suitable trimerization catalysts include all known trimerization catalysts such as phosphines, alkali metal salts, alkali metal alcoholates and tertiary amines. Preferred catalysts are the Mannich bases disclosed in DE-OS 2,452,532 (U.S. Pat. No. 3,996,223, herein incorporated by reference). Trimerization is continued until the concentration of unreacted starting diisocyanate, i.e., diisocyanates with no urethane or isocyanurate groups, in the mixture has fallen to less than 0.1 wt. %, based on the weight of the solution. This corresponds to the trimerization of about 50 to 60% of the isocyanate groups still present after urethanization.

Termination of the trimerization reaction is performed by adding a catalyst poison. Examples include sulphur when phosphines are used as catalysts and alkylating agents such as methyl toluenesulphonate when the preferred Mannich bases are used as catalysts. Also suitable as catalyst poisons are acylation agents such as benzoyl chloride.

The isocyanurate group-containing polyisocyanate solutions obtained in accordance with the process according to the invention have an NCO content of 12 to 17 wt. %, based on solids.

The products prepared by the process according to the invention demonstrate, for comparable solids contents and comparable residual monomer contents, substantially lower viscosities than the products from the prior art. This is demonstrated in the examples set forth below.

The polyisocyanates prepared by the process according to the invention are especially suitable as hardeners for two-component polyurethane coating compositions containing isocyanate-reactive compounds, preferably polyols, as the other binder component. They exhibit good compatibility with other commercially available lacquer binders and can easily be diluted with aromatic solvents.

In two-component polyurethane coating compositions, the products prepared by the process according to the invention impart outstanding drying characteristics, comparable with those of non-urethane-modified polyisocyanates.

The invention is further illustrated but is not intended to be limited by the following examples in which all parts and percentages are by weight unless otherwise specified.

EXAMPLES

In the following examples the viscosities were determined in a rotational viscometer as a single-point measurement in accordance with DIN 53 019 (HAAKE viscometer VT02, rotating body no. 1 ). The catalyst was a 40 wt. % solution in xylene of a Mannich base corresponding to the formula

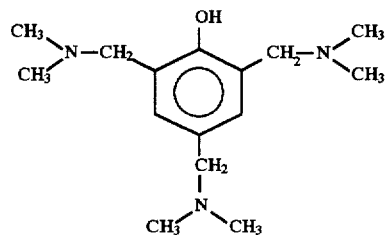

Example 1

477 g of 2,4-diisocyanatotoluene were initially introduced and heated to 60° C. 3.7 g of molten n-dodecanol were added at this temperature. Urethanization was performed at 60° C. until an NCO content of 47.7% was reached. Then the mixture was diluted with 480 g of butyl acetate, whereupon the mixture cooled down to 40° C. Trimerization was initiated at 40° C. by adding 1 g of catalyst solution. Trimerization was performed at a temperature of 40° C. Post-catalysis was performed by adding 0.4 g of catalyst solution every 12 hours and trimerization was continued until after about 48 h an NCO content of 7.5% was obtained.

To poison the catalyst, 2 g of methyl toluenesulphonate were added and the mixture was heated at 80° C. for 1 hour. A clear, pale yellow solution was obtained having the following characteristics:
Solids content: ca. 50%
Viscosity: 700 mPas (23° C.) (D=80.7 s$^{-1}$)
NCO content: 7.5%
Free diisocyanate content: 0.03%
Urethane group content: 0.36 mole % of the NCO groups were urethanized

Example 2

The procedure set forth in Example 1 was used except that 4.4 g of n-decanol was used as the monoalcohol. A solution of an isocyanurate group-containing polyisocyanate having the following characteristics was obtained:
Solids content: ca. 50%
Viscosity: 800 mPas (23° C.) (D=80.7 s$^{-1}$)
NCO content: 7.4%
Free diisocyanate content: <0.03% (limit of detection)
Urethane group content: 0.5 mole % of the NCO groups were urethanized.

Example 3

Comparison Example

The procedure set forth in Example 1 was used except that no monoalcohol was used. The resulting product had the following characteristics:
Solids content: ca. 50%
Viscosity: 1700 mPas (23° C.) (D=80.7 s$^{-1}$)
NCO content: 8.0%
Free diisocyanate content: 0.15%

Example 4

Comparison Example

The procedure set forth in Example 1 was used except that no monoalcohol was used. The resulting product had the following characteristics:
Solids content: ca. 50%

Viscosity: 6800 mPas (23° C.) (D=80.7 s$^{-1}$)
NCO content: 7.6%
Free diisocyanate content: 0.04%

Example 5

Comparison of the properties of a two-component polyurethane coating composition according to the invention with one not according to the invention The polyisocyanate solutions from Examples 1 and 3 were each combined at an NCO:OH equivalent ratio of 0.7:1 with a commercially available polyol having an OH content of 4.0% (Desmophen 1300, available from Bayer AG). A solids content of 45% was obtained by dilution with butylacetate.

Films were spread onto glass plates at a wet film thickness of 180 μm.

|  | Polyisocyanate solution from example 1 |  |  |  | Polyisocyanate solution from example 3 |  |  |  |
|---|---|---|---|---|---|---|---|---|
| Drying (min) (touch-dry, feels firm) | 33 |  |  |  | 33 |  |  |  |
| Flow time(s) in DIN-4-beaker at 23° C. |  |  |  |  |  |  |  |  |
| immediately | 17 |  |  |  | 18 |  |  |  |
| 2 h | 23 |  |  |  | 24 |  |  |  |
| 4 h | 36 |  |  |  | 39 |  |  |  |
| 6 h | 72 |  |  |  | 77 |  |  |  |
| Pendulum hardness |  |  |  |  |  |  |  |  |
| 4 h | 119 |  |  |  |  |  |  |  |
| 6 h | 150 |  |  |  | 118 |  |  |  |
| 1 d | 168 |  |  |  | 148 |  |  |  |
| 4 d | 182 |  |  |  | 167 |  |  |  |
| 7 d | 183 |  |  |  | 171 |  |  |  |
| Solvent resistance after curing for | *a | b | c | d | a | b | c | d |
| 8 h | **3 | 3 | 4 | 5 | 3 | 3 | 4 | 5 |
| 1 d | 1 | 1 | 1 | 5 | 1 | 1 | 2 | 5 |
| 4 d | 0 | 0 | 0 | 5 | 0 | 0 | 1 | 5 |
| 7 d | 0 | 0 | 0 | 5 | 0 | 0 | 0 | 5 |

* a) toluene, b) butyl acetate, c) MPA, d) acetone
** 0) unchanged, best value; 5) dissolves, poorest value The results obtained for the coating composition according to the invention are at least comparable to those obtained from the prior art coating composition. This demonstrates that the presence of urethane groups in the products according to the invention does not have a negative effect on the properties of the resulting coatings.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing isocyanurate group-containing polyisocyanates in lacquer solvents which are inert towards isocyanate groups which comprises a) reacting 0.2 to 1.5% of the NCO groups of a diisocyanate component containing
  i) 80 to 100 wt. %, based on the weight of the mixture, of 2,4-diisocyanatotoluene and
  ii) up to 20 wt. %, based on the weight of the mixture, of 2,6-diisocyanatotoluene, with a monohydric alcohol, R—OH, wherein R represents a linear or branched, saturated or unsaturated, aliphatic hydrocarbon group with 6 to 22 carbon atoms, to form urethanized diisocyanates, b) trimerizing at least a portion of the isocyanate groups of the urethanized diisocyanates in the form of 40 to 70 wt. % solutions in lacquer solvents which are inert towards isocyanate groups and in the presence of a catalyst for accelerating the trimerization of isocyanate groups, and c) terminating the trimerization reaction by adding a catalyst poison to obtain a reaction mixture having a free diisocyanatotoluene content of less than 0.1 wt. %, based on the weight of the reaction mixture.

2. The process of claim 1 wherein 0.2% to 1% of said NCO groups are reacted with said monohydric alcohol.

3. The process of claim 1 wherein said diisocyanate component consists essentially of 2,4-diisocyanatotoluene.

4. The process of claim 2 wherein said diisocyanate component consists essentially of 2,4-diisocyanatotoluene.

5. The process of claim 1 wherein R represents a linear or branched, saturated or unsaturated, aliphatic hydrocarbon group with 8 to 18 carbon atoms.

6. The process of claim 2 wherein R represents a linear or branched, saturated or unsaturated, aliphatic hydrocarbon group with 8 to 18 carbon atoms.

7. The process of claim 3 wherein R represents a linear or branched, saturated or unsaturated, aliphatic hydrocarbon group with 8 to 18 carbon atoms.

8. The process of claim 4 wherein R represents a linear or branched, saturated or unsaturated, aliphatic hydrocarbon group with 8 to 18 carbon atoms.

9. A two-component coating composition comprising the isocyanurate group-containing polyisocyanates made by the process of claim 1 and an isocyanate-reactive compound.

* * * * *